(12) United States Patent
Wang et al.

(10) Patent No.: US 9,399,609 B2
(45) Date of Patent: Jul. 26, 2016

(54) METHOD FOR MITIGATING HFC-245CB FORMATION DURING HCFO-1233XF HYDROFLUORINATION TO HCFC-244BB

(71) Applicant: HONEYWELL INTERNATIONAL INC., Morristown, NJ (US)

(72) Inventors: Haiyou Wang, Amherst, NY (US); Daniel C. Merkel, Orchard Park, NY (US); Hsueh Sung Tung, Getzville, NY (US); Haluk Kopkalli, Staten Island, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 14/203,823

(22) Filed: Mar. 11, 2014

(65) Prior Publication Data

US 2014/0275646 A1    Sep. 18, 2014

Related U.S. Application Data

(60) Provisional application No. 61/777,549, filed on Mar. 12, 2013.

(51) Int. Cl.
*C07C 17/07* (2006.01)
*C07C 17/21* (2006.01)
(Continued)

(52) U.S. Cl.
CPC ............ *C07C 17/23* (2013.01); *C07C 17/087* (2013.01); *C07C 17/206* (2013.01); *C07C 17/25* (2013.01)

(58) Field of Classification Search
CPC ...... C07C 17/21; C07C 17/206; C07C 17/07; C07C 17/087
See application file for complete search history.

(56) References Cited

U.S. PATENT DOCUMENTS

| 2,931,840 A | 4/1960 | Marquis et al. |
| 4,900,874 A | 2/1990 | Ihara et al. |

(Continued)

FOREIGN PATENT DOCUMENTS

| CN | 101597209 A | 12/2009 |
| CN | 101607865 A | 12/2009 |

(Continued)

OTHER PUBLICATIONS

International Search Report dated Jun. 24, 2014 issued in PCT/US2014/023000.

(Continued)

*Primary Examiner* — Jafar Parsa
*Assistant Examiner* — Medhanit Bahta
(74) *Attorney, Agent, or Firm* — Scully Scott Murphy and Presser

(57) ABSTRACT

The present process relates to a method for minimizing the formation of 1,1,1,2,2-pentafluoropropane in a liquid phase reaction of 2-chloro-3,3,3-trifluoropropene and HF in the presence of a hydrofluorination catalyst comprising:
(a) reacting HF with sufficient amount of 2-chloro-3,3,3-trifluoropropene in the presence of a hydrofluorination catalyst under conditions effective to form 2-chloro-1,1,1,2-tetrafluoropropane, the hydrofluorination catalyst being present in sufficient amounts to catalyze said reaction and the 2-chloro-1,1,1,2-tetrafluoropropane being formed with both a conversion of greater than 80% and a 1,1,1,2,2-pentafluoropropane selectivity lower than 20%; and
(b) maintaining the 2-chloro-1,1,1,2-tetrafluoropropane being formed with both a conversion of about 80% or more and a 1,1,1,2,2-pentafluoropropane selectivity of about 20% or less by adding said hydrofluorination catalyst to the reactor in small increments.

32 Claims, 1 Drawing Sheet

(51) Int. Cl.
*C07C 17/20* (2006.01)
*C07C 17/25* (2006.01)
*C07C 17/087* (2006.01)
*C07C 17/23* (2006.01)

(56) References Cited

U.S. PATENT DOCUMENTS

| | | |
|---|---|---|
| 8,058,486 B2 | 11/2011 | Merkel et al. |
| 8,084,653 B2 | 12/2011 | Tung et al. |
| 8,664,455 B2 | 3/2014 | Merkel et al. |
| 8,952,208 B2 | 2/2015 | Johnson et al. |
| 9,181,151 B2 | 11/2015 | Merkel et al. |
| 2009/0240090 A1 | 9/2009 | Merkel et al. |
| 2009/0312585 A1 | 12/2009 | Merkel et al. |
| 2010/0036179 A1* | 2/2010 | Merkel et al. ............... 570/156 |
| 2010/0331583 A1 | 12/2010 | Johnson et al. |
| 2011/0105807 A1 | 5/2011 | Kopkalli et al. |
| 2012/0184785 A1 | 7/2012 | Cottrell et al. |
| 2012/0215037 A1 | 8/2012 | Sun et al. |

FOREIGN PATENT DOCUMENTS

| | | |
|---|---|---|
| CN | 101665403 A | 3/2010 |
| JP | 2001-240569 A | 9/2001 |
| WO | WO 2012/056263 A1 | 5/2012 |

OTHER PUBLICATIONS

Banks, R. E. et al., Preparation of 2,3,3,3-tetrafluoropropene from trifluoroacetylacetone and sulphur tetrafluoroide, Journal of Fluorine Chemistry, (1997), vol. 82, pp. 171-174.

First Office Action issued in Chinese Patent Application No. 201480014570.4 dated Mar. 2, 2016 (in Chinese and English).

* cited by examiner

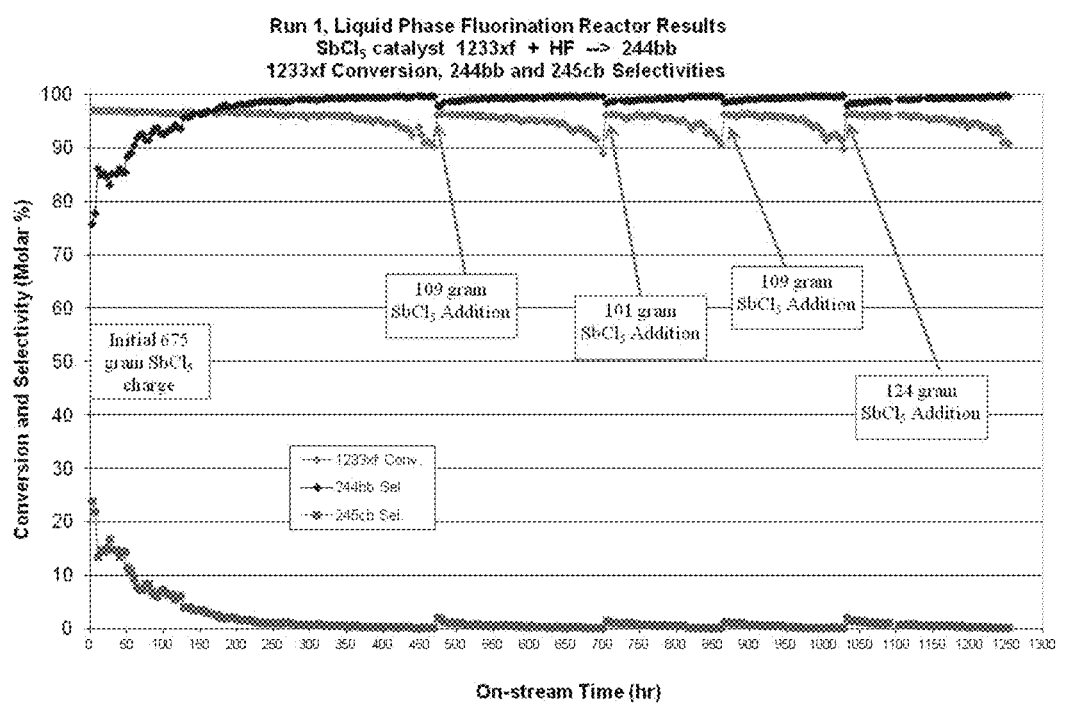

# METHOD FOR MITIGATING HFC-245CB FORMATION DURING HCFO-1233XF HYDROFLUORINATION TO HCFC-244BB

FIELD OF THE INVENTION

The present invention relates to an improved process for manufacturing 2-chloro-1,1,1,2-tetrafluoropropane (HCFC-244bb), and more particularly to an improved process for the production of HCFC-244bb from the reaction of 2-chloro-3,3,3-trifluoropropene (HCFO-1233xf) and hydrogen fluoride in a liquid phase reaction vessel in the presence of a liquid phase hydrofluorination catalyst. The HCFC-244bb is an intermediate in the production of 2,3,3,3-tetrafluoropropene (HFO-1234yf), which is a molecule with low global warming potential.

BACKGROUND OF THE INVENTION

Hydrofluoroolefins (HFOs), such as tetrafluoropropenes (including 2,3,3,3-tetrafluoropropene (HFO-1234yf)), are now known to be effective refrigerants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. HFO-1234yf has been shown to be a low global warming compound with low toxicity and, hence, can meet increasingly stringent requirements for refrigerants in mobile air conditioning. It has been found to be an effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid. Accordingly, compositions containing HFO-1234yf are among the materials being developed for use in many of the aforementioned applications. Thus, there is a need for new manufacturing processes for the production of tetrafluoropropenes and in particular 2,3,3,3-tetrafluoropropene.

Several methods of preparing HFOs are known. For example, U.S. Pat. No. 4,900,874 (Ihara et al.) describes a method of making fluorine containing olefins by contacting hydrogen gas with fluorinated alcohols. Although this appears to be a relatively high-yield process, commercial scale handling of hydrogen gas at high temperature is hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process, and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., Journal of Fluorine Chemistry, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

A manufacturing process for HFO-1234yf, as disclosed in U.S. Pat. No. 8,058,486, uses 1,1,2,3-tetrachloropropene (HCO-1230xa) as starting raw material. The process consists of the following three steps: 1) HCO-1230xa+HF→2-chloro-3,3,3-trifluoropropene (HCFO-1233xf)+HCl in a vapor phase reactor charged with a solid hydrofluorination catalyst such as fluorinated chromia, 2) HCFO-1233xf+HF→2-chloro-1,1,1,2-tetrafluoropropane (HCFC-244bb) in a liquid phase reactor charged with a liquid hydrofluorination catalyst such as fluorinated $SbCl_5$, and 3) HCFC-244bb→HFO-1234yf in a vapor phase reactor. One issue encountered in the operation of Step 2 is the formation of 1,1,1,2,2-pentafluoropropane (HFC-245cb), which can cause significant yield loss in long term. Thus, there is a need for means by which the formation of HFC-245cb can be reduced.

SUMMARY OF THE INVENTION

The present invention relates to a process for the production of 2-chloro-1,1,1,2-tetrafluoropropane (HCFC-244bb), which comprises reacting 2-chloro-3,3,3,-trifluoropropene (HCFO-1233xf) with hydrogen fluoride, in a liquid phase reaction vessel in the presence of a liquid phase hydrofluorination catalyst. The invention provides an improved process for producing 2-chloro-1,1,1,2-tetrafluoropropane (HCFC-244bb), in which HCFO-1233xf conversion is maintained at higher than about 80%, while simultaneously minimizing the formation of 1,1,1,2,2-pentafluoropropane. In another embodiment, the HCFO-1233xf conversion is greater than about 90%, and in another embodiment, greater than about 95%. This improved conversion is effected by periodical addition of fresh hydrofluorination catalyst in small increments. The addition of fresh hydrofluorination catalyst occurs continuously or periodically.

More specifically, the present process relates to a method for minimizing the formation of 1,1,1,2,2-pentafluoropropane in a liquid phase reaction of 2-chloro-3,3,3-trifluoropropene and HF in the presence of a hydrofluorination catalyst comprising:

(a) reacting HF with sufficient amount of 2-chloro-3,3,3-trifluoropropene in the presence of a hydrofluorination catalyst under conditions effective to form 2-chloro-1,1,1,2-tetrafluoropropane, the hydrofluorination catalyst being present in sufficient amounts to catalyze said reaction, wherein the 2-chloro-1,1,1,2-tetrafluoropropane is formed with a conversion of about 80% or higher and wherein 1,1,1,2,2-pentafluoropropane selectivity is about 20% or lower; and (b) maintaining the 2-chloro-1,1,1,2-tetrafluoropropane being formed with both a conversion of about 80% or more and a 1,1,1,2,2-pentafluoropropane selectivity of about 20% or less by adding said hydrofluorination catalyst continuously or periodically in increment amounts.

For example, in an embodiment, the formation of 1,1,1,2,2-pentafluoropropane is minimized by (a) reacting HF with sufficient amount of 2-chloro-3,3,3-trifluoropropene in the presence of a hydrofluorination catalyst to form 2-chloro-1,1,1,2-tetrafluoropropane, the hydrofluorination catalyst being present in sufficient amounts to catalyze said reaction, wherein the 2-chloro-1,1,1,2-tetrafluoropropane is formed with a conversion of about 80% or higher and wherein 1,1,1,2,2-pentafluoropropane selectivity is about 20% or lower; and (b) maintaining the 2-chloro-1,1,1,2-tetrafluoropropane being formed with both a conversion of about 80% or more and a 1,1,1,2,2-pentafluoropropane selectivity of about 20% or less by adding said hydrofluorination catalyst periodically in an amount ranging from about 0.5% to about 10% by weight of the total weight of the catalyst and HF in the reactor. In an embodiment, the addition of hydrofluorination catalyst is periodic, as described herein, while in another embodiment, the addition of hydrofluorination catalyst is continuous.

However, there is a maximum amount of catalyst that could be added. The maximum amount added is 98% by weight relative to the total weight of HF and catalyst.

BRIEF DESCRIPTION OF THE DRAWINGS

The following FIGURE is exemplary of the results of the process when conducted in accordance with the description herein. The present invention is not to be construed as being limited by the FIGURE.

FIG. 1 depicts the conversion of 1233xf and the selectivity of 244bb and the selectivity of 245cb over time from the periodic addition of $SbCl_5$ catalyst in the liquid phase fluorinate reaction of 1233xf+HF→244bb. The dark line in the figures represents 244bb selectivity while the top light line represents 1233xf conversion and the bottom line represents 245cb selectivity.

DETAILED DESCRIPTION OF THE INVENTION

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

The term "dehydrochlorinating", "dehydrochlorination" or "dehydrochlorinated", as used herein, means a process during which hydrogen and chlorine on adjacent carbons in a molecule are removed.

The term "alkyl", as used herein, either alone or in combination includes cyclic or acyclic and straight-chain or branched alkyl groups, such as, methyl, ethyl, n-propyl, propyl, or the different isomers thereof. It includes, for example, straight or branched chain alkyl groups containing from 1 to 6 carbon atoms and cyclic alkyl groups containing 3 to 6 ring carbon atoms and up to a total of 10 carbon atoms.

The term "hydrofluoroolefin", as used herein, means a molecule containing hydrogen, carbon, fluorine, and at least one carbon-carbon double bond.

As used herein, the terms "fluorination catalyst" and "hydrofluorination catalyst" are synonymous and are used interchangeably.

The term, "in small increments", as used herein, refers to the amount of hydrofluorination catalyst that is added to the reactor to maintain both the conversion of 2-chloro-3,3,3-trifluoropropene to 2-chloro-1,1,1,2-tetrafluoropropane and the 1,1,1,2,2-pentafluoropropane selectivity to the desired level.

By the term "desired level", it is meant that the conversion of 2-chloro-3,3,3-trifluoropropene to 2-chloro-1,1,1,2-tetrafluoropropane is at a specific objective level ranging from about 80% to about 100% conversion and that the 1,1,1,2,2-pentafluoropropane selectivity ranges from about 20% to about 0%.

The term "periodically", or periodic or synonym thereto, when referring to the addition of hydrofluorination catalyst as used herein, denotes that the hydrofluorination catalyst is added each time to the reactor when the conversion of 2-chloro-3,3,3-trifluoropropene to 2-chloro-1,1,1,2-tetrafluoropropane falls below the desired level.

The term "continuously" or "continuous", or synonym thereto, when referring to the addition of hydrofluorination catalyst, denotes that the hydrofluorination catalyst is being constantly added in small increments, obviously smaller than when the addition is periodic. The rate of addition that the hydrofluorination catalyst is added is described herein.

The present process is an intermediate step in the preparation of 2,3,3,3-tetrafluoropropene (HFO-1234yf). It relates to the hydrofluorination of 2-chloro-3,3,3-trifluoropropene to form 2-chloro-1,1,1,2-tetrafluoropropane. The production of 2-chloro-1,1,1,2-tetrafluoropropane (HCFC-244bb), in the present process, requires reacting 2-chloro-3,3,3-trifluoropropene (HCFO-1233xf) with hydrogen fluoride, in a liquid phase reaction vessel and a liquid phase hydrofluorination catalyst to thereby produce HCFC-244bb. The reaction is conducted in a batch or continuous mode.

In accordance with the process of the present invention, HCFO-1233xf is converted to 2-chloro-1,1,1,2-tetrafluoropropane (HCFC-244bb). In one embodiment, this step may be performed in the liquid phase in a liquid phase reactor. Any reactor suitable for a hydrofluorination reaction may be used in the invention. The reactor is constructed from materials which are resistant to the corrosive effects of HF such as Hastelloy-C, Inconel, Monel and fluoropolymer-lined vessels. Such liquid phase hydrofluorination reactors are well known in the art.

Any substantially pure liquid phase fluorination catalyst may be used in the invention. By substantially pure, it denotes that the catalyst contains a minimum of impurities. In one embodiment, it is greater than 90% pure; in another embodiment, it is greater than 95% pure; while in another embodiment, it is greater than 98% pure. A non-exhaustive list of liquid phase fluorination catalysts include Lewis acids, such as transition metal halides, transition metal oxides, Group IVb metal halides, a Group Vb metal halides, or combinations thereof. Non-exclusive examples of liquid phase fluorination catalysts are antimony halide, tin halide, tantalum halide, titanium halide, niobium halide, molybdenum halide, iron halide, fluorinated chrome halide, fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. In another embodiment, the fluorination catalyst is antimony pentachloride.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

In the practice of the present invention, a liquid phase catalyst as described below is charged into a hydrofluorination reactor prior to heating the reactor. Then the HF and the HCFO-1233xf are fed to the reactor after the reactor reaches the desired temperature. The reaction is conducted under effective reaction conditions. For example, the reaction is conducted at a temperature ranging from about 30° C. to about 200° C., while in another embodiment, it is conducted in a temperature ranging from about 50° C. to about 150° C., and, in another embodiment, at a temperature ranging from about 75° C. to about 125° C. The pressure of the reaction varies depending on the temperature, quantity of hydrogen fluoride used, and conversion of HCFO-1233xf. Convenient operating pressure ranges from about 5 psig to about 200 psig in one embodiment, while in another embodiment, from about 30 psig to about 175 psig, and, in still another embodiment, from about 60 psig to about 150 psig.

The HF and the 2-chloro-3,3,3-trifluoropropene are present in concentrations effective for the conversion to 2-chloro-1,1,1,2-tetrafluoropropane. Based on reaction stoichiometry, the required mole ratio of HF to HCFO-1233xf is at least equal to the number of double bonds in the starting organic material and, in another embodiment, the mole ratio of HF to HCFO-1233xf is present in an excess. In an embodiment, the mole ratio of HF to HCFO-1233xf ranges from about 1:1 to about 50:1, while in another embodiment, it ranges from about 1:1 to about 30:1 and, in still another embodiment, it ranges from about 2:1 to about 15:1. Any water in the HF will react with and deactivate the catalyst. Therefore substantially anhydrous HF is preferred. By "substantially anhydrous" is meant that the HF contains about 0.05 weight % water or less. In an embodiment, the HF contains about 0.02 weight % water or less. However, one of ordinary skill in the art will appreciate that the presence of water in the catalyst can be compensated for by increasing the amount of catalyst used.

One of the side products of the reaction is the formation of 1,1,1,2,2-pentafluoropropane (HFC-245cb). The objective is to minimize the formation of 1,1,1,2,2-pentafluoropropane. This objective is important for several reasons. First, the formation of 1,1,1,2,2-pentafluoropropane decreases the yield of 2-chloro-1,1,1,2-tetrafluoropropane. Moreover, the formation of 1,1,1,2,2-pentafluoropropane interferes with the efficiency of the overall process to form 2,3,3,3-tetrafluoropropene (HFO-1234yf), and a separate step must be employed to separate 1,1,1,2,2-pentafluoropropane from 2-chloro-1,1,1,2-tetrafluoropropane (HCFC-244bb) so that the latter compound can be dehydrohalogenated to form 2,3,3,3-tetrafluoropropene (HFO-1234yf) in the next step of the overall process, as defined herein. Thus, it is important to find a means of decreasing the amount of 1,1,1,2,2-pentafluoropropane formed in this reaction.

The present inventors have found that the formation of 1,1,1,2,2-pentafluoropropane is minimized if the reaction is conducted as described herein. More specifically, the formation of 1,1,1,2,2-pentafluoropropane in a liquid phase reaction of 2-chloro-3,3,3-trifluoropropene and HF in the presence of a hydrofluorination catalyst is minimized if the reaction is conducted by (a) reacting HF with sufficient amount of 2-chloro-3,3,3-trifluoropropene in the presence of a hydrofluorination catalyst under conditions effective to form 2-chloro-1,1,1,2-tetrafluoropropane, the hydrofluorination catalyst being present in sufficient amounts to catalyze said reaction and the 2-chloro-1,1,1,2-tetrafluoropropane being formed with both a conversion of about 80% or more and a 1,1,1,2,2-pentafluoropropane selectivity of about 20% or less; and (b) maintaining the 2-chloro-1,1,1,2-tetrafluoropropane being formed with both a conversion of about 80% or more and a 1,1,1,2,2-pentafluoropropane selectivity of about 20% or less by adding hydrofluorination catalyst continuously or periodically in increment amounts. In an embodiment, the addition of hydrofluorination catalyst is periodically as described herein while in another embodiment the addition of hydrofluorination catalyst is continuous.

In the present process, in an embodiment, the amount of 2-chloro-1,1,1,2-tetrafluoropropane formed is monitored periodically to determine the yield of 2-chloro-1,1,1,2-tetrafluoropropane or the amount of conversion of 2-chloro-3,3,3-trifluoropropene In one embodiment, if the amount of yield of 2-chloro-1,1,1,2-tetrafluoropropane is about 80% or less, additional catalyst is added to the reaction, as described herein. The amount of yield and conversion is determined by techniques known in the art, such as by taking a small aliquot of sample formed in the reaction from the reactor and injecting it into a gas chromatograph and comparing the amounts of 2-chloro-1,1,1,2-tetrafluoropropane, 1,1,1,2,2-pentafluoropropane, and 2-chloro-3,3,3-trifluoropropene and any other products formed, as measured by GC (FID) area.

In another embodiment, additional catalyst is added if the amount of yield or conversion to 2-chloro-1,1,1,2-tetrafluoropropane is about 90% or less. In other embodiment, additional catalyst is added if the amount of yield or conversion to 2-chloro-1,1,1,2-tetrafluoropropane is about 95% or less.

When additional catalyst is added, in an embodiment, it is added to the location in the reactor where the reaction is taking place. It is, in one embodiment, added to the reactor on the same side as the reactants are added. For example, if the reactants, i.e., HF and 2-chloro-3,3,3-trifluoropropene is added to the top of the reactor, the catalyst is added at the top of the reactor, i.e., it is top-charged into the reactor.

When catalyst is to be added to the reactor, in accordance with the present invention, it is added continuously or periodically in small increments. In an embodiment, when added in small increments as described herein below it is added so that the concentration of the catalyst is increased about 10 wt % or less, based on the total weight of the catalyst and HF in the reactor. This amount is easily determined because the amount of catalyst and HF in the reactor is based on the amount of HF and catalyst that was added into the reactor. Thus, for example if additional catalyst is to be added to the reactor, and the amount of catalyst added is 25 grams and the amount of HF added is 75 grams, the amount of catalyst to be added is less than 10 grams, which is less than 10% by weight, based on the total weight of catalyst and HF in the reactor.

In another embodiment, if catalyst is to be added periodically, it is added in an amount of about 5 wt % or less, based on the total weight of the catalyst and HF. In still another embodiment, if catalyst is to be added periodically, it is added in an amount of 3 wt or less, based on the total weight of the catalyst and HF. However, if catalyst is to be added periodically, a minimum of about 0.5 wt % is added based on the total weight of the catalyst and HF in the reactor. Thus, in an embodiment, the amount of catalyst added is 10%, 9.5%, 9%, 8.5%, 8.0%, 7.5%, 7.0%, 6.5%, 6.0%, 5.5%, 5.0%, 4.5% 4.0%, 3.5%, 3.0%, 2.5%, 2.0%, 1.5%, 1.0% or 0.5% by weight, based on the total weight of the catalyst and HF added to the reactor.

The amount of hydrofluorination catalyst added periodically may or may not increase each time by the same percentage relative to the total weight of the catalyst and HF in the reactor. In an embodiment, the increase in catalyst each time added is the same percentage, while in another embodiment, the increase added periodically is a different percentage. Regardless, the amount of catalyst added is in the range described herein. The amount of catalyst added each time is dependent on the desired level of conversion of 2-chloro-3,3,3-trifluoropropene to 2-chloro-1,1,1,2-tetrafluoropropane.

In one embodiment, the catalyst is present in an ionic liquid. Liquid ionic based catalysts are well known in the art. See, for example, WO 2008/149011 and WO 01/81353. Ionic liquids based catalysts are prepared by techniques known in the art. In an embodiment, the ionic liquid based catalysts are obtained by reaction of at least one halogenated or oxyhalogenated Lewis acid based on, for example, aluminum, titanium, niobium, tantalum, tin, antimony, nickel, zinc or iron with a salt of general $Y^+A^-$, where $A^-$ denotes a halide anion, such as bromide, iodide, chloride or fluoride and $Y^+$ denotes a quaternary ammonium cation, quaternary phosphonium cation or ternary sulfonium cation.

For example, antimony based ionic liquids, such as antimony pentachloride, are prepared from the reaction product of $SbOCl_3$ and tetra-n-butylammonium chloride using techniques known in the art.

The catalyst may be added batchwise or continuously. If added continuously, in an embodiment, it is added at a rate of about 0.03 wt % or less per hour, based on the total weight of the catalyst and the HF. In another embodiment, it is added to the reactor at a rate of about 0.01 wt % or less per hour, and in another embodiment, it is added at a rate of about 0.005 wt % or less per hour, based on the total weight of the HF and catalyst.

It has been found that when the catalyst is added in small increments, in accordance with the present invention, the conversion of 2-chloro-3,3,3-trifluoropropene to 2-chloro-1,1,1,2-tetrafluoropropane is noticeably increased, while the selectivity to 1,1,1,2,2-pentafluoropropane remains at the desired level. In particular, it has been found that the reaction can be run for tens or hundreds of hours while maintaining a high conversion of 2-chloro-3,3,3-trifluoropropene to 2-chloro-1,1,1,2-tetrafluoropropane and a low selectivity of 1,1,1,2,2-pentafluoropropane. For example, using the process in accordance with the present invention, the conversion of 2-chloro-3,3,3-trifluoropropene to 2-chloro-1,1,1,2-tetrafluoropropane can be achieved from about 80% to about 98%, for example, 80%, 81%, 82%, 83%, 84%, 85%, 86%, 87%, 88%, 89%, 90%, 91%, 92%, 93%, 94%, 95%, 96%, 97%, 98%. Moreover, using the process in accordance with the present process, the selectivity of 1,1,1,2,2-pentafluoropropane can range from about 20% to about 0.5%, such as 20%, 19%, 18%, 17%, 16%, 15%, 14%, 13%, 12%, 11%, 10%, 9%, 8%, 7%, 6%, 5%, 4%, 3%, 2%, 1%, 0.5% or lower. For several tens and hundreds of hours, the reaction can achieve any of these levels, whatever level is desired. The yield of 2-chloro-1,1,1,2-tetrafluoropropane is controlled, to some extent, as to when additional catalyst is added. For example, the yield is greatest when the catalyst is added when the selectivity to 1,1,1,2,2-pentafluoropropane is less than 5%. Thus, a desired yield and conversion to 2-chloro-1,1,1,2-tetrafluoropropane can be controlled, to some extent, as to when the catalyst is added to the reaction.

After the reaction proceeds for a period of time, catalyst deactivation starts to occur so that the conversion of 2-chloro-3,3,3,-trifluoropropene to 2-chloro-1,1,1,2-tetrafluoropropane begins to decrease. As catalyst deactivation occurs, fresh hydrofluorination catalyst is added to the reactor in small increments, as described herein, to maintain HCFO-1233xf conversion at the levels described herein. Catalyst deactivation means the decrease of HCFO-1233xf conversion over time on stream. Catalyst may be added, in an embodiment, after the reaction is stopped (both HF and HCFO-1233xf feeds are stopped). In another embodiment, catalyst is added after the reactor pressure is somewhat decreased. In some embodiments, catalyst is added after the majority of HF inventory in the reactor is further removed. In another embodiment, catalyst is added while the reaction is on-going. The catalyst is added in a way that its concentration is increased in the increment as described herein.

No more additional catalyst is added to the reactor when a total of about 98% by weight of catalyst has been added to the reactor, based on the total weight of the catalyst and HF. The reaction is allowed to proceed until the level of conversion to 2-chloro-1,1,1,2-tetrafluoropropane is less than the desired conversion to 2-chloro-1,1,1,2-tetrafluoropropane, for example in one embodiment, when it is about 80% or less, in another embodiment, about 90% or less and in another embodiment, about 95% or less. At this juncture, in some embodiment, the catalyst is regenerated by flowing a stream of chlorine through the catalyst. In some embodiments, the catalyst is partially or completely removed from the reactor using techniques known in the art, and either new catalyst is added and/or the remaining catalyst is regenerated using techniques known in the art, for example, as described herein.

Then the reaction is restarted. When the conversion to 2-chloro-1,1,1,2-tetrafluoropropane is about 80% or less, or about 90% or less or about 95% or less, additional catalyst is added in small increments, in accordance with the present invention.

The present inventors have also found that the amount of conversion to 2-chloro-1,1,1,2-tetrafluoropropane is enhanced and the amount of 1,1,1,2,2-pentafluoropropane is decreased if the hydrofluorination is initiated with a fluorination catalyst present in a concentration of about 50 wt % or less. As defined above, the weight percentage of catalyst is the weight percentage of the fluorination catalyst relative to the total weight of the catalyst and HF in the reactor. In another embodiment, the catalyst is initially present in about 40 wt % or less, and in still another embodiment, it is present in about 25 wt % or less. However, the catalyst that is present is a minimum concentration of about 2 wt % initially to effect the hydrofluorination of 2-chloro-3,3,3-trifluoropropene to 2-chloro-1,1,1,2-tetrafluoropropane. Thus, to initiate the reaction, the hydrofluorination catalyst is present in an amount ranging from about 2 wt % to about 50 wt %, based on the total weight of the catalyst and HF in the reactor. In another embodiment, the catalyst is initially present in an amount ranging from about 10 wt % to about 40 wt %, based on the total weight of the catalyst and HF in the reactor, and still in another embodiment, the catalyst is present in an amount ranging from about 15 wt % to about 25 wt %, based on the total weight of catalyst and HF in the reactor. For example, in an embodiment, the hydrofluorination of HCFO-1233xf is initiated with a Sb-catalyst (SbCl$_5$ as initial form) concentration is about 50 wt % or less, in another embodiment, about 40 wt % or less, and in another embodiment, at about 25 wt % or less, to achieve the desired initial catalyst performance. The catalyst concentration is defined as the weight percentage of SbCl$_5$ catalyst in the total weight of SbCl$_5$ catalyst and HF in reactor. The desired initial catalyst performance is defined as an HCFO-1233xf conversion of about 80% or more, in one embodiment, or about 90% or more in another embodiment, and in still another embodiment, about 95% or more. Additionally, it is defined as an HFC-245cb selectivity of about 20% or less, in one embodiment, about 10% or less, in another embodiment, and about 5% or less, in still another embodiment. When the conversion to 2-chloro-1,1,1,2-tetrafluoropropane is less than the desired amount, the catalyst concentration is then increased continuously or periodically in small increments, as described herein.

The resulting HCFC-244bb, as well as unconverted HCFO-1233xf and HF may be recovered from the reaction mixture via any separation or purification method known in the art such as neutralization and distillation. The HCFC-244bb can be used in pure form, or optionally in partially pure form or impure form with the entire effluent from the HCFC-244bb production step used as an intermediate in the production of 2,3,3,3-tetrafluoropropene HFO-1234yf. The process of the invention may be carried out either in a batch or continuous mode. In a continuous process, the HCFO-1233xf, and HF are preferably fed simultaneously to the reactor after the reactor reaches the desired temperature. The temperature and pressure of the hydrofluorination reaction remain essentially the same for both the batch and continuous modes of operation. The residence time or contact time, varies from about 1 second to about 2 hours, preferably from about 5 seconds to about 1 hour and more preferably from about 10 seconds to about 30 minutes. A sufficient quantity of catalyst must be present to effect the hydrofluorination in the residence times described above. In a continuous mode of operation, HF, HCFO-1233xf, and HCFC-244bb are continuously removed from the reactor.

It is understood that when the catalyst is added, in accordance with the present invention, the other parameters described hereinabove remain the same. More specifically, the temperatures, pressures, mole ratio of HF to HCFO-1233xf, and any other parameters discussed hereinabove are in the ranges described herein. This invention contemplates that new catalyst to be added is the same or different from the catalyst present in the reactor, either originally, or in the previous addition. Nevertheless, in an embodiment, the catalyst added is the same as originally present, and that in each addition of catalyst, the catalyst added is the same as originally present in the reactor for this reaction.

As described above, the fluorination process of the present invention is an intermediate process for preparing tetrafluoropropenes, including 2,3,3,3-tetrafluoropropene (HFO-1234yf).

Step 1A:

Step 1B:

Step 1C:

Step 2:

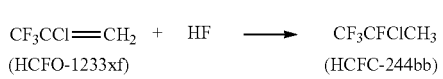

Step 3:

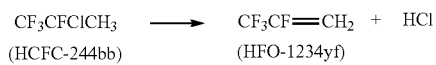

In the first step of the reaction, the chlorohydrocarbon is reacted with HF in the presence of a catalyst under fluorination conditions to produce CF$_3$CCl═CH$_2$ (HCFO 1233xf). Three alternative reactions are provided, each with different starting materials. In one reaction, 1,1,2,3-tetrachloropropene is the starting material; in the second reaction, 2,3,3,3-tetrachloropropene is the starting material; while in the third reaction, 1,1,1,2,3-pentachloropropane is the starting material. In the third alternative the 1,1,1,2,3-pentachloropropane not only is fluorinated, but the reactant is also dehydrochlorinated to produce 2-chloro-3,3,3-trifluoropropene (HCFO-1233xf). The second step of the reaction is the fluorination of HCFO-1233xf in the presence of a catalyst to produce 2-chloro-1,1,1,2-tetrafluoropropane (HCFC-244bb). The third reaction step is in the dehydrochlorination of HCFC-244bb to produce 2,3,3,3-tetrafluoropropene (HFO-1234yf).

In the second step of the process, the 2-chloro-3,3,3-trifluoropropene (1233xf) is hydrofluorinated to form 2-chloro-1,1,1,2-tetrafluoropropane (244bb), which is then dehyrochlorinated to form the refrigerant 2,3,3,3-tetrafluoropropene (HFO-1234yf). One of the effects of the present process is to minimize the formation of 1,1,1,2,2-pentafluoropropane (245cb), for the formation of 245cb interferes with and makes it more difficult to conduct the dehydrochlorination reaction to form 2,3,3,3-tetrafluoropropene (HFO-1234yf). However, by maintaining the reaction under the reaction conditions described hereinabove, the present process minimizes the formation of 1,1,1,2,2-pentafluoropropane (245cb) and CF$_3$CHClCH$_2$F (1,1,1,3-terafluoro-2-chloropropane) and maximizes the formation of the desired product CF$_3$CClFCH$_3$.

Thus, another aspect of the present process is to prepare tetrafluoropropenes, including 2,3,3,3-tetrafluoropropene (HFO-1234yf).

According to one embodiment, the present invention includes a manufacturing process for making 2,3,3,3-tetrafluoroprop-1-ene using a starting material according to formula I:

$$CX_2\!=\!CCl\!-\!CH_2X \qquad \text{(Formula I)}$$

$$CX_3\!-\!CCl\!=\!CH_2 \qquad \text{(Formula II)}$$

$$CX_3\!-\!CHCl\!-\!CH_2X \qquad \text{(Formula III)}$$

wherein X is independently selected from F, Cl, Br, and I, provided that at least one X is not fluorine. In certain embodiments, the compound(s) of Formula I contains at least one chlorine, a majority of the Xs as chlorine, or all Xs as chlorine. In certain embodiments, the compound(s) of formula I include 1,1,2,3-tetrachloropropene (HCO-1230xa).

The method generally includes at least three reaction steps. In the first step, a starting composition of Formula I (such as 1,1,2,3-tetrachloropropene) is reacted with anhydrous HF in a first vapor phase reactor (fluorination reactor) to produce a mixture of 2-chloro-3,3,3-trifluoropropene (1233xf) and HCl. In certain embodiments, the reaction occurs in the vapor phase in the presence of a vapor phase catalyst, such as, but not limited to, a fluorinated chromium oxide. The catalyst may (or may not) have to be activated with anhydrous hydrogen fluoride (hydrogen fluoride gas) before use depending on the state of the catalyst.

While fluorinated chromium oxides are disclosed as the vapor phase catalyst, the present invention is not limited to this embodiment. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures and any one of which may be optionally fluorinated. In one embodiment, the catalyst is chrome oxide, such as for example, $Cr_2O_3$. Co-catalysts may also be present. Combinations of catalysts suitable for the first fluorination step nonexclusively include $Cr_2O_3$, $FeCl_3/C$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. In one embodiment, the chrome oxide is present with a co-catalyst for fluorination reaction. Chromium oxide/aluminum oxide catalysts are described in U.S. Pat. No. 5,155,082, the contents of which are incorporated herein by reference. Chromium catalysts are also described in U.S. Pat. No. 3,258,500, the contents of which are also incorporated by reference. In another embodiment, Chromium (III) oxides such as crystalline chromium oxide or amorphous chromium oxide are used as catalysts, while in another aspect of the present invention, the catalyst for this fluorination step is amorphous chromium oxide. One such chromium oxide catalyst that is used in the first fluorination step is the activated chromium oxide gel catalyst, described in U.S. Pat. No. 3,258,500. Chromium oxide ($Cr_2O_3$) is a commercially available material which may be purchased in a variety of particle sizes.

The first fluorination reaction, according to the present invention, may be carried out under atmospheric pressure. In another embodiment, this reaction may be carried out under pressures of less than or greater than atmospheric pressures. For example, the process may be carried out, in one embodiment at a pressure ranging from about 0 psig to about 200 psig and in another embodiment from about 5 psig to about 100 psig.

The first fluorination reaction is conducted under conditions effective for the conversion to 1233xf. In an embodiment, the temperature of the process may range from about 150° C. to about 400° C., in another embodiment from about 180° C. to about 400° C. In another embodiment, the temperature of the process ranges from about 180° C. to about 400° C., while in another embodiment, the temperature of the process is conducted from about 200° C. to about 300° C.

When the compound of formula I is 1,1,2,3-tetrachloropropene (HCO-1230xa), the mole ratio of HF to 1230xa in step 1 of the reaction ranges from about 1:1 to about 50:1 and, in certain embodiments, from about 10:1 to about 20:1. The reaction between HF and HCO-1230xa is carried out at a temperature from about 150° C. to about 400° C. (in certain embodiments, about 180° C. to about 300° C.) and at a pressure of about 0 psig to about 200 psig (in certain embodiments from about 5 psig to about 100 psig). Contact time of the 1230xa with the catalyst may range from about 1 second to about 60 seconds, however, longer or shorter times can be used.

The second step of the process is the hydrofluorination of 2-chloro-3,3,3-trifluoropropene (HCFO-1233xf), as described herein, to form 2-chloro-1,1,1,2-tetrafluoropropane (HCFC-244bb). Typically, 2-chloro-1,1,1,2-tetrafluoropropane (HCFC-244bb) produced is first recovered from the product mixture and then used as raw material for the next step.

The third step of the present process is the dehydrochlorination of 2-chloro-1,1,1,2-tetrafluoropropane (HCFC-244bb). In the third step of 1234yf production, the 244bb is fed to a second vapor phase reactor (dehydrochlorination reactor) to be dehydrochlorinated to make the desired product 2,3,3,3-tetrafluoroprop-1-ene (1234yf). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form.

Metal halide or metal oxide catalysts may include, but are not limited to, mono-, bi-, and tri-valent metal halides, oxides and their mixtures/combinations thereof. Component metals include, but are not limited to $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625. In an embodiment, the dehydrochlorination can be conducted in a reactor made of the aforementioned alloys without the addition of solid catalysts.

The dehydrochlorination reaction is conducted under effective conditions. In some embodiments of this invention, 2-chloro-1,1,1,2-tetrafluoropropane (HCFC-244bb) is carried out at a temperature of from about 200° C. to about 700° C. to produce a product mixture comprising 2,3,3,3-tetrafluoropropene (HFO-1234yf). In another embodiment, the reaction temperature for the dehydrochlorination reaction is about 300 to about 550° C. In an embodiment, the reaction pressure ranges from about 0 to about 150 psig.

The reactor effluent may be fed to a caustic scrubber or to a distillation column to remove the by-product of HCl, to produce an acid-free organic product which, optionally, may undergo further purification using one or any combination of purification techniques that are known in the art.

In some embodiments of this invention, the dehydrochlorination process is carried out by reacting 2-chloro-1,1,1,2- tetrafluoropropane (HCFC-244bb) with a basic aqueous solution to produce a product mixture comprising 2,3,3,3-tetrafluoropropene (HFO-1234yf). As used herein, the basic aqueous solution is a liquid that is primarily an aqueous liquid having a pH of over 7; the liquid may be a solution, dispersion, emulsion, suspension or the like. In some embodiments of this invention, the basic aqueous solution has a pH of 8 or higher. In some embodiments of this invention, the basic aqueous solution has a pH of 10 or higher. In some embodiments of this invention, an inorganic base is used to form the basic aqueous solution. Such inorganic base can be selected from the group consisting of hydroxide, oxide, carbonate, and phosphate salts of alkali, alkaline earth metals and mixtures thereof. In some embodiments, such inorganic base is sodium hydroxide, potassium hydroxide, or mixtures thereof. In some embodiments of this invention, the basic aqueous solution is an aqueous solution of a quaternary ammonium hydroxide of the formula $NR_4OH$ wherein each R is independently hydrogen, a $C_1$ to $C_{16}$ alkyl group, aralkyl group, or substituted alkyl group, provided that not all R are hydrogens. Examples of $NR_4OH$ compounds useful in this invention are tetra-n-butylammonium hydroxide, tetra-n-propylammonium hydroxide, tetraethylammonium hydroxide, tetramethylammonium hydroxide, benzyltrimethylammonium hydroxide, hexadecyltrimethyammonium hydroxide, and choline hydroxide. Optionally, 2-chloro-1,1,1,2-tetrafluoropropane (HCFC-244bb) is reacted with the basic aqueous solution in the presence of an organic solvent. In some embodiments of this invention, the organic solvent is selected from the group consisting of benzene and its derivatives, alcohols, alkyl and aryl halides, alkyl and aryl nitriles, alkyl, alkoxy and aryl ethers, ethers, amides, ketones, sulfoxides, phosphate esters and mixtures thereof. Optionally, 2-chloro-1,1,1,2-tetrafluoropropane (HCFC-244bb) is reacted with the basic aqueous solution in the presence of a phase transfer catalyst. As used herein, a phase transfer catalyst is intended to mean a substance that facilitates the transfer of ionic compounds into an organic phase from an aqueous phase or from a solid phase. The phase transfer catalyst facilitates the reaction between water-soluble and water-insoluble reaction components. In some embodiments of this invention, the phase transfer catalyst is selected from the group consisting of crown ethers, onium salts, cryptands, polyalkylene glycols, and mixtures and derivatives thereof. The phase transfer catalyst can be ionic or neutral.

The reactors, packings, distillation columns, and their associated feed lines, effluent lines, and associated units used in applying the processes of embodiments of this invention may be constructed of materials resistant to corrosion. Typical materials of construction include Teflon™ materials and glass. Typical materials of construction also include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The following are examples of the invention and are not to be construed as limiting.

Example 1

A Teflon™-lined liquid phase reactor (Teflon is a trademark of E.I. du Pont de Nemours & Co) equipped with a 2-inch ID catalyst stripper (a packed column to keep catalyst from escaping from the reactor system) was used for the following two experiments. The reactor dimension is 2.75-inch ID×36-inch L (length).

520 grams of $SbCl_5$ catalyst and 5 lbs of HF were added to the reactor to provide an approximately 19 wt % concentration of catalyst. The reactor was heated to 87-90° C. at a pressure of 100 psig when the HF and organic feeds were started. The organic (2.0 GC area % HFC-245cb, 5.0 GC area % HCFC-244bb, and 92.9 GC area % HCFO-1233xf feed) was fed at 0.6 lb/hr and the HF was 0.4 lb/hr. The reaction was run at these conditions for about 10 hours. The reactor effluent was sampled after the scrubber for a total of 9 times during the experiment. The amount of HFC-245cb produced was decreased from initially approximately 7.0 GC area % to finally 4.9 GC area %, and the amount of unconverted HCFO-1233xf was slightly decreased from initially 6.5 GC area % to finally 4.7 GC area %, indicating catalyst performance was gradually improved with time on stream.

Comparative Example 1

The same liquid phase reactor as described in Example 1 was used. 4175 grams of $SbCl_5$ and 5 lbs of HF were added to the reactor to provide a ~65 wt % concentration of catalyst. The organic (98 GC area % HCFO-1233xf feed) was fed at 0.408 lb/hr and the HF was 0.495 lb/hr. The reactor temperature range for the experiment was 78-91° C. and the pressure range was 85 psig-115 psig. The reaction was continuously run for about 136 hours. As in the first experiment, the reactor effluent was sampled after the scrubber for GC analysis. The results show after 2.5 h on stream, the HCFO-1233xf conversion was 97.7%, and the selectivities to HFC-245cb and HCFC-244bb were 40.2 and 52.8%, respectively.

In summary, the results of Example 1 and Comparative Example 1 shows the initial catalyst concentration have significant impact on the initial HFC-245cb selectivity and low initial HFC-245cb selectivity can be realized by using low catalyst concentration.

Example 2

The same liquid phase reactor as described in Example 1 was used. 0.98 kg of $SbCl_5$ catalyst was charged and 7 lbs of HF was added during catalyst fluorination step. The HCFO-1233xf hydrofluorination was then started under conditions of 85-90° C., 100 psig, and average feed rates of 0.5-0.6 lb/h org and 0.3-0.4 lb/h HF ('approximately 4/1 of HF/HCFO-1233xf mole ratio). After 37 hours on stream, 0.19 kg fresh $SbCl_5$ catalyst was top-charged into reactor, which brought catalyst concentration from initially about 24% to about 27%, which is approximately 3% increase. The reaction was then re-started. The GC analysis of reactor effluent samples indicates the HCFO-1233xf conversion was increased from approximately 36.6% (at $36^{th}$ hour) to approximately 94.8% (at $38^{th}$ hour) after top-charging 0.19 kg fresh $SbCl_5$ catalyst, while HFC-245cb selectivity was only slightly increased from about 0.04% to about 1.32%. After 228 hours on stream, 0.06 kg fresh $SbCl_5$ catalyst was top-charged into the reactor, which brought catalyst concentration from previously amount of about 27% to about 28%, which is about 1% increase. The reaction was then re-started. The GC analysis of reactor effluent samples indicated that the HCFO-1233xf conversion was increased from approximately 78.5% (at $229^{th}$ hour) to 94.5% (at $232^{th}$ hour) after top-charging 0.06 kg fresh $SbCl_5$ catalyst, while HFC-245cb selectivity was only slightly increased from about 0.08% to about 0.16%.

Comparative Example 2

The same liquid phase reactor as described in Example 1 was used.

0.86 kg of SbCl$_5$ catalyst was charged and 7 lbs of HF was added during catalyst fluorination step. The HCFO-1233xf hydrofluorination was then started under conditions of 85-90° C., 100 psig, and average feed rates of 0.5-0.6 lb/h org and 0.3-0.4 lb/h HF ('~4/1 of HF/HCFO-1233xf mole ratio). After 110 hours on stream, 0.62 kg fresh SbCl$_5$ catalyst was top-charged into reactor, which brought catalyst concentration from initially ~21% to ~35%, almost 14% increase. The reaction was then re-started. The GC analysis of reactor effluent samples indicates the HCFO-1233xf conversion was increased from ~71.4% (at 108$^{th}$ hour) to 96.5% (at 111$^{th}$ hour) after top-charging 0.62 kg fresh SbCl$_5$ catalyst, while HFC-245cb selectivity was sharply increased from 0.1% to 21.6%.

In summary, the results from Example 2 and Comparative Example 2 show the sharp increase in HFC-245cb selectivity when top-charging catalyst can be avoided by using small catalyst increment rate.

Example 3

A Teflon™-lined liquid phase reactor (Teflon is a trademark of E.I. du Pont de Nemours & Co) equipped with a 2-inch ID catalyst stripper (a packed column to keep catalyst from escaping from the reactor system) was used for the following experiment. The reactor dimension is 3.75-inch ID×36-inch L (length) and is equipped with a slow RPM agitator. The reactor was heated by applying steam to a jacket surrounding the reaction vessel.

675 grams of SbCl$_5$ and 2725 grams of anhydrous HF were initially charged to the reactor (20 wt % SbCl$_5$) and slowly agitated. The reactor was then heated with steam to about 90° C. at a pressure of about 100 psig. A continuous feed of anhydrous HF at a rate of about 0.4 lb/hr was initiated followed by a continuous feed of HCFO-1233xf at a rate of about 0.9 lb/hr. Reaction products and some unreacted HF were allowed to continuously exit the top of the catalyst stripper column where they were analyzed periodically by GC. The 245cb selectivity was initially 23%, dropping to <5% in 128 hours and <2% in 180 hrs. The 1233xf conversion was initially about 97% and remained relatively stable (ave-96.6%) for first 350 hrs at which time it started to decrease gradually, but noticeably and after 400 hrs the rate of decrease accelerated further. The average 1233xf conversion for the length of the initial 468 hr portion of the run was 95.97% while the average 245cb and 244bb selectivities were 3.80% and 96.14% respectively After 469 hrs when the conversion of 1233xf had decreased to about 92% a 109 gram SbCl$_5$ top charge was added to the reactor without de-inventorying the reactor. Upon restart the 1233xf conversion was initially 96.4% and the 245cb selectivity spiked to 2.0% and each gradually decreased over the length of this portion of the run. The reactor was on-stream for 230 hours after the first catalyst top charge before the conversion of 1233xf decreased to below 92%. The 1233xf conversion averaged 95.1% and the 245cb and 244bb selectivities averaged 0.62% and 99.36% respectively for the 230 hours. Continuous feeds of anhydrous HF at a rate of about 0.4 lb/hr and HCFO-1233xf at a rate of about 0.9 lb/hr were maintained along with the original reaction temperature and pressure. Total on-stream time for the experiment was 699 hours at this point.

After 699 hrs when the conversion of 1233xf had decreased to about 92% a 101 gram SbCl$_5$ top charge was added to the reactor without de-inventorying the reactor. 1233xf feed containing no 1232xf was initially used as feed after catalyst top charge. Upon restart the 1233xf conversion was initially 96.5% and the 245cb selectivity spiked to 1.5% and each gradually decreased over the length of this portion of the run. The reactor was on-stream for 162 hours after the second catalyst top charge before the conversion of 1233xf decreased to below 92%. The 1233xf conversion averaged 95.1% and the 245cb and 244bb selectivities averaged 0.65% and 99.32% respectively for the 162 hours. Continuous feeds of anhydrous HF at a rate of about 0.4 lb/hr and HCFO-1233xf at a rate of about 0.9 lb/hr were maintained along with the original reaction temperature and pressure. Total on-stream time for the experiment was 861 hours at this point.

After 861 hrs when the conversion of 1233xf had decreased to about 92% a 109 gram SbCl$_5$ top charge was added to the reactor without de-inventorying the reactor. Upon restart the 1233xf conversion was initially 96.4% and the 245cb selectivity spiked to 1.3% and each gradually decreased over the length of this portion of the run. The reactor was on-stream for 166 hours after the third catalyst top charge before the conversion of 1233xf decreased to below 92%. The 1233xf conversion averaged 95.0% and the 245cb and 244bb selectivities averaged 0.55% and 99.42% respectively for the 166 hours. Continuous feeds of anhydrous HF at a rate of about 0.4 lb/hr and HCFO-1233xf at a rate of about 0.9 lb/hr were maintained along with the original reaction temperature and pressure. Total on-stream time for the experiment was 1027 hours at this point.

After 1027 hrs when the conversion of 1233xf had decreased to about 92% a 124 gram SbCl$_5$ top charge was added to the reactor without de-inventorying the reactor. Upon restart the 1233xf conversion was initially 96.4% and the 245cb selectivity spiked to 2.1% and each gradually decreased over the length of this portion of the run. The reactor was on-stream for 226 hours after the fourth top charge before the conversion of 1233xf decreased to below 92%. The 1233xf conversion averaged 95.15% and the 245cb and 244bb selectivities averaged 0.81% and 99.16% respectively for the 230 hours. Continuous feeds of anhydrous HF at a rate of about 0.4 lb/hr and HCFO-1233xf at a rate of about 0.9 lb/hr were maintained along with the original reaction temperature and pressure. The total on-stream time for the experiment was 1253 hours. 1233xf conversion, selectivity data for the major products, 245cb and 244bb, and events that happened during the experiment can be found in FIG. 1.

Example 4

The same reactor that was used for Example 3 is used for a second experiment. 715 grams of SbCl$_5$ and 2850 grams of anhydrous HF are initially charged to the reactor (20 wt % SbCl$_5$) and slowly agitated. The reactor is then heated with steam to about 90° C. at a pressure of about 100 psig. A continuous feed of anhydrous HF at a rate of about 0.5 lb/hr is initiated followed by a continuous feed of HCFO-1233xf at a rate of about 1.1 lb/hr. Reaction products and some unreacted HF are allowed to continuously exit the top of the catalyst stripper column where they are analyzed periodically by GC. The 245cb selectivity is initially 21%, dropping to <5% in 140 hours and <2% in 205 hrs. Conversely, as the 245cb selectivity is decreasing the 244bb selectivity is increasing from about 78.5% to >98%. The 1233xf conversion is initially about 97.3% and remains relatively stable (ave 97%) for the first 205 hrs. At this point a continuous co-feed of fresh SbCl$_5$ catalyst is initiated at a rate of about 0.6 grams/hr and is fed into the vapor space of reactor. With this catalyst addition rate the selectivity of 245cb is maintained at <2% while the 1233xf conversion remains constant at about 97% for the next 500 hours that the experiment is run.

Many aspects and embodiments have been described above and are merely exemplary and not limiting. After reading this specification, skilled artisans appreciate that other aspects and embodiments are possible without departing from the scope of the invention.

What is claimed is:

1. A method for minimizing the formation of 1,1,1,2,2-pentafluoropropane in a liquid phase reaction of 2-chloro-3,3,3-trifluoropropene and HF in the presence of a hydrofluorination catalyst in a reactor comprising:
   (a) reacting HF with sufficient amount of 2-chloro-3,3,3-trifluoropropene in the presence of a hydrofluorination catalyst under conditions effective to form 2-chloro-1,1,1,2-tetrafluoropropane, the hydrofluorination catalyst being present in sufficient amounts to catalyze said reaction and 2-chloro-1,1,1,2-tetrafluoropropane being formed with both a conversion of about 80% or more and 1,1,1,2,2-pentafluoropropane selectivity of about 20% or less; and
   (b) maintaining the 2-chloro-1,1,1,2-tetrafluoropropane being formed with both a conversion of about 80% or more and a 1,1,1,2,2-pentafluoropropane selectivity of about 20% or less by adding said hydrofluorination catalyst continuously or periodically to the reactor in small increments.

2. The method according to claim 1 wherein the hydrofluorination catalyst is added periodically in an amount ranging from about 0.5 wt % to about 10 wt % based on the total weight of the hydrofluorination catalyst and HF present in the reactor.

3. The method according to claim 1 wherein the initial catalyst concentration in step (a) ranges from about 2 wt % to about 50 wt %, based on the total weight of catalyst and HF in the reactor.

4. The method according to claim 1 wherein the initial catalyst concentration in step (a) ranges from about 10 wt % to about 40 wt %, based on the total weight of catalyst and HF in the reactor.

5. The method according to claim 1 wherein the initial catalyst concentration in step (a) ranges from about 15 wt % to about 25 wt %, based on the total weight of catalyst and HF in the reactor.

6. The method according to claim 2 wherein the catalyst is added periodically in an amount ranging from about 1 wt % to about 5 wt % or less, based on the total weight of HF and catalyst in the reactor.

7. The method according to claim 2 wherein the catalyst is added periodically in an amount ranging from about 2 wt % to about 3 wt %, based on the total weight of HF and catalyst in the reactor.

8. The method according to claim 1 wherein the hydrofluorination catalyst is antimony halide, a tin halide, a tantalum halide, a titanium halide, a niobium halide, and molybdenum halide, an iron halide, a fluorinated chrome halide, a fluorinated chrome oxide or combinations thereof.

9. The method according to claim 8 wherein the hydrofluorination catalyst is $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combination thereof.

10. The method according to claim 1 wherein the reaction is conducted at a temperature ranging from about 30° C. to about 200° C.

11. The method according to claim 1 wherein the reaction is conducted at a temperature ranging from about 50° C. to about 150° C.

12. The method according to claim 1 wherein the reaction is conducted at a temperature ranging from about 75° C. to about 125° C.

13. The method according to claim 1 wherein the mole ratio of HF to 2-chloro-3,3,3-trifluoropropene ranges from about 1:1 to about 50:1.

14. The method according to claim 1 wherein the mole ratio of HF to 2-chloro-3,3,3-trifluoropropene ranges from about 1:1 to about 30:1.

15. The method according to claim 1 wherein the mole ratio of HF to 2-chloro-3,3,3-trifluoropropene ranges from about 2:1 to about 15:1.

16. The method according to claim 1 wherein the hydrofluorination catalyst is antimony pentachloride.

17. A method for preparing 2,3,3,3-tetrafluoroprop-1-ene comprising:
   (a) providing a starting composition comprising at least one compound having a structure selected from Formulas I, II and III:

  Formula I
   $$CX_2=CCl-CH_2X \qquad \text{Formula I}$$

  Formula II
   $$CX_3-CCl=CH_2 \qquad \text{Formula II}$$

  Formula III
   $$CX_3-CHCl-CH_2X \qquad \text{Formula III}$$

wherein each X is independently F, Cl, Br or I, provided that at least one X is not fluorine:
   (b) contacting said starting composition with a first hydrofluorinating agent to produce a first intermediate composition comprising 2-chloro-3,3,3-trifluoropropene;
   (c) reacting HF with sufficient amount of 2-chloro-3,3,3-trifluoropropene in the presence of a second hydrofluorination catalyst under conditions effective to form 2-chloro-1,1,1,2-tetrafluoropropane, the second hydrofluorination catalyst being present in sufficient amounts to catalyze said reaction and 2-chloro-1,1,1,2-tetrafluoropropane being formed with both a conversion of at least 80% and 1,1,1,2,2-pentafluoropropane selectivity of at most 20%; and
   (d) maintaining the 2-chloro-1,1,1,2-tetrafluoropropane being formed with both a conversion of about 80% or more and a 1,1,1,2,2-pentafluoropropane selectivity of about 20% or less by adding said second hydrofluorination catalyst to the reactor periodically or continuously in small increments; and
   (e) dehydrochlorinating 2-chloro-1,1,1,2-tetrafluoropropane to produce a reaction product comprising 2,3,3,3-tetrafluoroprop-1-ene.

18. The method according to claim 17 wherein the second hydrofluorination catalyst is added periodically in an amount ranging from about 0.5 wt % to about 10 wt % based on the total weight of the hydrofluorination catalyst and HF present in the reactor.

19. The method according to claim 17 wherein the initial concentration of said second hydrofluorination catalyst in step (c) ranges from about 2 wt % to about 50 wt %, based on the total weight of catalyst and HF in the reactor.

20. The method according to claim 17 wherein the initial concentration of said second hydrofluorination catalyst in step (c) ranges from about 10 wt % to about 40 wt %, based on the total weight of catalyst and HF in the reactor.

21. The method according to claim 17 wherein the initial concentration of said second hydrofluorination catalyst in step (c) ranges from about 15 wt % to about 25 wt %, based on the total weight of catalyst and HF in the reactor.

22. The method according to claim 17 wherein said second hydrofluorination catalyst is added periodically in an amount ranging from about 1 wt % to about 5 wt % or less, based on the total weight of HF and catalyst in the reactor.

23. The method according to claim 17 wherein said second hydrofluorination catalyst is added periodically in an amount ranging from about 2 wt % to about 3 wt % or less, based on the total weight of HF and catalyst in the reactor.

24. The method according to the claim 1 wherein the hydrofluorination catalyst is added continuously at a rate of 0.03 wt % or less per hour based on the total weight of the catalyst and HF.

25. The method according to claim 24 where the hydrofluorination catalyst is added at a rate of about 0.01 wt % or less per hour, based on the total weight of the catalyst and HF.

26. The method according to claim 25 wherein the hydrofluorination catalyst is added at a rate of about 0.005 wt % or less per hour, based on the total weight of the catalyst and HF.

27. The method according to claim 16 wherein the hydrofluorination catalyst is added at a rate of about 0.03 wt % or less per hour, based on the total weight of the catalyst and HF.

28. The method according to claim 27 wherein the hydrofluorination catalyst is added at a rate of about 0.01 wt % or less per hour, based on the total weight of the catalyst and HF.

29. The method according to claim 28 wherein the hydrofluorination catalyst is added at a rate of about 0.005 wt % or less per hour, based on the total weight of the catalyst and HF.

30. The method according to claim 17 wherein the hydrofluorination catalyst is added at a rate of about 0.03 wt % or less per hour, based on the total weight of the catalyst and HF.

31. The method according to claim 30 wherein the hydrofluorination catalyst is added at a rate of about 0.01 wt % or less per hour, based on the total weight of the catalyst and HF.

32. The method according to claim 31 wherein the hydrofluorination catalyst is added at a rate of about 0.005 wt % or less per hour, based on the total weight of the catalyst and HF.

\* \* \* \* \*